(12) United States Patent
Gill et al.

(10) Patent No.: US 9,358,303 B2
(45) Date of Patent: *Jun. 7, 2016

(54) COMPOUNDS CONTAINING A VASCULAR DISRUPTING AGENT

(71) Applicant: Incanthera Limited, Bradford (GB)

(72) Inventors: Jason Gill, Bradford (GB); Paul Loadman, Bradford (GB); Rob Falconer, Bradford (GB); Laurence Patterson, Bradford (GB); Jennifer Xavier, Needingworth (GB); Michael Bibby, Bradford (GB)

(73) Assignee: Incanthera Ltd, Bradford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/109,333

(22) Filed: Dec. 17, 2013

(65) Prior Publication Data

US 2014/0179592 A1 Jun. 26, 2014

Related U.S. Application Data

(63) Continuation of application No. 12/595,482, filed as application No. PCT/GB2008/001043 on Mar. 27, 2008, now Pat. No. 8,691,751.

(30) Foreign Application Priority Data

Apr. 12, 2007 (GB) .................................. 0707034.5

(51) Int. Cl.
*A61K 47/42* (2006.01)
*A61K 47/48* (2006.01)
*C07K 7/06* (2006.01)

(52) U.S. Cl.
CPC ......... *A61K 47/48338* (2013.01); *A61K 47/481* (2013.01); *A61K 47/48215* (2013.01); *C07K 7/06* (2013.01)

(58) Field of Classification Search
None
See application file for complete search history.

(56) References Cited

U.S. PATENT DOCUMENTS

| | | |
|---|---|---|
| 2003/0195152 A1 | 10/2003 | Suarato et al. |
| 2006/0074008 A1 | 4/2006 | Senter et al. |
| 2007/0117133 A1 | 5/2007 | Trieu et al. |
| 2011/0275554 A1 | 11/2011 | Falconer et al. |

FOREIGN PATENT DOCUMENTS

| | | |
|---|---|---|
| EP | 1862470 A1 | 12/2007 |
| WO | WO-0168145 A2 | 9/2001 |
| WO | WO-02072620 A1 | 9/2002 |
| WO | WO-2005023314 A1 | 3/2005 |
| WO | WO-2006079120 A2 | 7/2006 |
| WO | WO-2006090813 A1 | 8/2006 |
| WO | WO-2006110476 A2 | 10/2006 |
| WO | WO-2008125800 A2 | 10/2008 |

OTHER PUBLICATIONS

Hollebecque et al. "Vascular disrupting agents: a delicate balance" Current Opinion Oncology, 2012, 24(3), 305-315.*
Egeblad et al. "New Functions for the Matrix Metalloproteinases in Cancer Progression" Nature Reviews Cancer, 2002, vol. 2, 161-174.*
Albright et al. "Matrix metalloproteinase—activated doxorubicin prodrugs" Mol Cancer Ther May 2005 4; 751-760.*
Atkinson et al. "Development of a Novel Tumor-Targeted Vascular" Cancer Res Sep. 1, 2010 70; 6902-6912.*
"Abnormal Hemoglobins." *Biochemistry*. Voet et al., eds. New York: John Wiley & Sons, Inc. (1995):235-241.
"analog." On-line Medical Dictionary. Mar. 5, 2000. Web. Jul. 7, 2005. http://cancerweb.ncl.ac.uk/cgi-bin/omd?query=analog.
"derivative." On-line Medical Dictionary. Nov. 18, 1997. Web. Jul. 7, 2005. http://cancerweb.ncl.ac.uk/cgi-bin/omd?query=derivative.
"Designing Custom Peptides." Sigma Genosys. Web. Dec. 16, 2004. http://www.sigma-genosys.com/peptide_design.asp.
Berendsen et al. "A Glimpse of the Holy Grail?" *Science*. 282.5389(1998):642-643.
Bradley et al. "Limits of Cooperativity in a Structurally Modular Protein: Response of the Notch Ankyrin Domain to Analogous Alanine Substitutions in Each Repeat." *J. Mol. Biol.* 324(2002):373-386.
Hooper et al. "Identification and Development of Vascular Disrupting Agents: Natural Products That Interfere with Tumor Growth." *Natural Products and Cancer Drug Discovery*. Koehn, ed. New York: Springer Science. (2013):17-38.
Ngo et al. "Computational Complexity, Protein Structure Prediction, and the Levinthal Paradox." *The Protein Folding Problem and Tertiary Structure Production*. Merz, Jr., et al., eds. Boston: Birkhauser. (1994):491-506.
Rudinger. "Characteristics of the Amino Acids as Components of a Peptide Hormone Sequence." *Peptide Hormones*. Parsons, ed. Baltimore, MD: University Park Press. (1976):1-7.
"Matrix Metalloproteinases." *MMP*. (2007):1-15.
Aitkhozhina et al. "10-Amino Analogs of Colchicine: Synthesis, Structure, and Biological Activity." *Bioorganicheskaia Khimia*. 22.5(1996):383-386. (Russian Original and English Abstract).
Albright et al. "Matrix-Metalloproteinase-Activated Doxorubicin Prodrugs Inhibit HT1080 Zenograft Growth Better than Doxorubicin with Less Toxicity." *Mol. Cancer Therapeutics*. 4. 5(2005):751-760.
Beerepoot et al. "Phase I Clinical Evaluation of Weekly Administration of the Novel Vascular-Targeting Agent, ZD6126, in Patients with Solid Tumors." *J. Clin. Oncol.* 24.10(2006):1491-1498.
Chau et al. "Synthesis and Characterization of Dextran-Peptide-Methotrexate Conjugates for Tumor Targeting via Mediation by Matrix Metalloproteinase II and Matrix Metalloproteinase IX." *Bioconj. Chem.* 15.4(2004):931-941.
Chaudhuri et al. "The Interaction of the B-ring of Colchicine with α-Tubulin: A Novel Footprinting Approach." *J. Mol. Biol.* 303.5(2000):679-692.
Davis et al. "ZD6126: A Novel Vascular-Targeting Agent that Causes Selective Destruction of Tumor Vasculature." *Cancer Res.* 62.24(2002):7247-7253.

(Continued)

*Primary Examiner* — Christina Bradley
(74) *Attorney, Agent, or Firm* — Mintz Levin Cohn Ferris Glovsky and Popeo, P.C.; Muriel Liberto, Esq.

(57) ABSTRACT

The present invention relates to compounds, and pharmaceutically acceptable salts thereof, comprising a vascular disrupting agent (VDA) associated and a MMP proteolytic cleavage site. The compounds are useful in the treatment of cancer.

17 Claims, 3 Drawing Sheets

(56) References Cited

OTHER PUBLICATIONS

Denekamp. "Endothelial Cell Proliferation as a Novel Approach to Targeting Tumour Therapy." *Br. J. Cancer.* 45(1982):136-139.

Dubowchik et al. "Receptor-Mediated and Enzyme-Dependent Targeting of Cytotoxic Anticancer Drugs." *Pharmacol. Therapeutics.* 83(1999):67-123.

Esbolaev et al. "C-10 Amino Acid Derivatives of Colchicine." *Chem. Nat. Compounds.* 28.3-4(1992):325-328.

Esbolaev et al. "C-10 Dipeptide Derivatives of Colchicine." *Khimiya Prirodnykh Soedinenii.* 1(1989):91-95. (Russian Original and English Abstract).

Esbolaev et al. "Cytotoxic Activity of Dipeptide Derivatives of Colchicine." *Izvestiya Akademii Nauk Kazakhskoi SSR.* 5(1989):83-86. (Russian Original and English Abstract).

Hamel. "Antimitotic Natural Products and Their Interactions with Tubulin." *Med. Res. Rev.* 16.2(1996):207-231.

Kline et al. "Novel Antitumor Prodrugs Designed for Activation by Matrix Metalloproteinases-2 and -9." *Mol. Pharma.* 1.1(2004):9-22.

Kratz et al. "Development and In Vitro Efficacy of Novel MMP2 and MMP9 Specific Doxorubicin Albumin Conjugates." Bioorg. Med. Chem.Lett. 11.15(2001):2001-2006.

Kratz et al. "Prodrugs of Anthracyclines in Cancer Chemotherapy." Curr. Med. Chem. 13.5(2006):477-523.

Lippert. "Vascular Disrupting Agents." *Bioorg. Med. Chem.* 15.2(2007):605-615.

Mansour et al. "A New Approach for the Treatment of Malignant Melanoma: Enhanced Antitumor Efficacy of an Albumin-Binding Doxorubicin Prodrug that is Cleaved by Matrix Metalloproteinase 2." *Cancer Res.* 63.14(2003):4062-4066.

Nagase et al. "Human Matrix Metalloproteinase Specificity Studies using Collagen Sequence-Based Synthetic Peptides." *Biopolymers.* 40(1996):399-416.

Quinn et al. "Toxicity Quantitative Structure—Activity Relationships of Colchicines." *J. Med. Chem.* 24.5(1981):636-639.

*Remington's Pharmaceutical Sciences.* Gennaro, ed. Easton, PA: Mack Publishing Co. (1985):1418.

Rustin et al. "Phase I Clinical Trial of Weekly Combretastatin A4 Phosphate: Clinical and Pharmacokinetic Results." *J. Clin. Oncol.* 21.15(2003):2815-2822.

Siemann et al. "Differentiation and Definition of Vascular-Targeted Therapies." *Clin. Cancer Res.* 11(2005):416-420.

Tozer et al. "Disrupting Tumour Blood Vessels." *Nat. Rev. Cancer.* 5.6(2005):423-435.

\* cited by examiner

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: MMP proteolytic cleavage site
<220> FEATURE:
<221> NAME/KEY: MOD_RES
<222> LOCATION: (1)..(1)
<223> OTHER INFORMATION: Citrulline
<220> FEATURE:
<221> NAME/KEY: MOD_RES
<222> LOCATION: (3)..(3)
<223> OTHER INFORMATION: Homo phenylalanine

<400> SEQUENCE: 1

Arg Gly Phe Tyr Leu
1               5

<210> SEQ ID NO 2
<211> LENGTH: 7
<212> TYPE: PRT
<213> ORGANISM: Artificial Sequence
<220> FEATURE:
<223> OTHER INFORMATION: MMP proteolytic cleavage site
<220> FEATURE:
<221> NAME/KEY: misc_feature
<222> LOCATION: (1)..(1)
<223> OTHER INFORMATION: Where X may be selected from Citrulline
      Arginine, Glycine, Glutamine or Proline.
<220> FEATURE:
<221> NAME/KEY: misc_feature
<222> LOCATION: (2)..(2)
<223> OTHER INFORMATION: Where X may be selected from Citrulline
      Arginine, Glycine, Glutamine or Proline.
<220> FEATURE:
<221> NAME/KEY: MOD_RES
<222> LOCATION: (3)..(3)
<223> OTHER INFORMATION: Citrulline
<220> FEATURE:
<221> NAME/KEY: MOD_RES
<222> LOCATION: (5)..(5)
<223> OTHER INFORMATION: Homo Phenylalanine

<400> SEQUENCE: 2

Xaa Xaa Arg Gly Phe Tyr Leu
1               5

<210> SEQ ID NO 3
<211> LENGTH: 7
<212> TYPE: PRT
<213> ORGANISM: Artificial Sequence
<220> FEATURE:
<223> OTHER INFORMATION: MMP proteolytic cleavage site
<220> FEATURE:
<221> NAME/KEY: MOD_RES
<222> LOCATION: (3)..(3)
<223> OTHER INFORMATION: Citrulline
<220> FEATURE:
<221> NAME/KEY: MOD_RES
<222> LOCATION: (5)..(5)
<223> OTHER INFORMATION: Homo Phenylalanine

<400> SEQUENCE: 3

Glu Pro Arg Gly Phe Tyr Leu
1               5

<210> SEQ ID NO 4
<211> LENGTH: 7
<212> TYPE: PRT
```

```
<213> ORGANISM: Artificial Sequence
<220> FEATURE:
<223> OTHER INFORMATION: MMP proteolytic cleavage site
<220> FEATURE:
<221> NAME/KEY: MOD_RES
<222> LOCATION: (3)..(3)
<223> OTHER INFORMATION: Citrulline
<220> FEATURE:
<221> NAME/KEY: MOD_RES
<222> LOCATION: (5)..(5)
<223> OTHER INFORMATION: Homo Phenylalanine

<400> SEQUENCE: 4

Arg Ser Arg Gly Phe Tyr Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Endopeptidase-activated pro-drugs
<220> FEATURE:
<221> NAME/KEY: MOD_RES
<222> LOCATION: (1)..(1)
<223> OTHER INFORMATION: beta-Alanine
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (6)..(6)
<223> OTHER INFORMATION: Homo phenylalanine

<400> SEQUENCE: 5

Ala Glu Pro Arg Gly Phe Tyr Leu Tyr
1               5

<210> SEQ ID NO 6
<211> LENGTH: 9
<212> TYPE: PRT
<213> ORGANISM: Artificial Sequence
<220> FEATURE:
<223> OTHER INFORMATION: Pro-drug intermediate
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (6)..(6)
<223> OTHER INFORMATION: Homo phenylalanine

<400> SEQUENCE: 6

Ala Glu Pro Arg Gly Phe Tyr Leu Tyr
1               5

<210> SEQ ID NO 7
<211> LENGTH: 9
<212> TYPE: PRT
<213> ORGANISM: Artificial Sequence
<220> FEATURE:
<223> OTHER INFORMATION: MMP-activated prodrug
<220> FEATURE:
<221> NAME/KEY: MOD_RES
<222> LOCATION: (4)..(4)
<223> OTHER INFORMATION: Citrulline
<220> FEATURE:
<221> NAME/KEY: MOD_RES
<222> LOCATION: (6)..(6)
<223> OTHER INFORMATION: Homo phenylalanine
```

```
<400> SEQUENCE: 7

Ala Arg Ser Arg Gly Phe Tyr Leu Tyr
1               5
```

COMPOUNDS CONTAINING A VASCULAR DISRUPTING AGENT

RELATED APPLICATIONS

This application is a continuation of U.S. application Ser. No. 12/595,482, which is a national stage application, filed under 35 U.S.C. §371, of International Application no. PCT/GB2008/001043, filed on Mar. 27, 2008, which claims priority to GB Application No. 0707034.5, filed on Apr. 12, 2007. The contents of each of these applications are herein incorporated by reference in their entireties.

INCORPORATION-BY-REFERENCE OF SEQUENCE LISTING

The contents of the text file named "41303-501C01US_ST25.txt", which was created on Mar. 5, 2014 and is 3 KB in size, is hereby incorporated by reference in their entirety.

FIELD OF THE INVENTION

The present invention relates to compounds that are activated in vivo from relatively biologically inactive compounds, so called "prodrugs", to relatively biologically active compounds. The invention also relates to the use of such compounds in the targeted treatment of cancer.

BACKGROUND TO THE INVENTION

The clinical utility of many anti-tumour compounds is restricted by their toxicity towards healthy cells, resulting in a narrow therapeutic index and subsequent reduction in treatment benefit. Therefore, it would be advantageous to target the drug selectively to the tumour and consequently reduce normal tissue toxicity and side effects. One means of approaching this objective is the design of prodrug molecules that are specifically targeted to or selectively activated in tumour tissue, thereby reducing systemic levels of active drug and increasing the therapeutic index.

Tumour growth, survival and dissemination of metastatic tumour cells is dependent on the presence of a functioning vascular network within the tumour (Tozer et al., Nat Rev Cancer, 5, 423-435 (2005)). Disruption of even a small proportion of the tumour vasculature has been demonstrated to induce wide ranging tumour death and retardation of metastasis, since a single blood vessel is responsible for supporting the survival of many tumour cells. Endothelial cells, which form the major component of the vasculature, are highly dependent upon the tubulin cytoskeleton for their motility, invasion, attachment, alignment and proliferation (Denekamp, J, Br J Cancer, 45, 136-139 (1982)). Agents which disrupt the endothelial microtubule network will therefore cause a rapid collapse in tumour blood flow and a prolonged period of vascular shutdown, culminating in extensive tumour-cell necrosis (Tozer et al., Nat Rev Cancer, 5, 423-435 (2005); Lippert J W, Bioorg Med Chem, 15, 605-615 (2007)).

Colchicine and its analogues are potent vascular disrupting agents (VDA) causing haemorrhage and subsequent extensive necrosis in tumours (Tozer et al., Nat Rev Cancer, 5, 423-435 (2005)), as a direct consequence of tubulin binding and induction of microtubule depolymerisation (Chaudri et al., J Mol Biol, 303, 679-692 (2000)). Colchicine has not, however, shown intrinsic value as a clinically applicable anticancer therapeutic due to a high level of toxicity and consequent very narrow therapeutic index (Tozer et al., Nat Rev Cancer, 5, 423-435 (2005); Quinn et al., J Med Chem, 24, 636-639 (1981)). Major efforts in several laboratories have focused on development of small molecule VDAs with clinical potential, notably ZD6126 (phosphate analogue of N-acetylcolchinol) and combretastatin-A4-phosphate (Lippert J W, Bioorg Med Chem, 15, 605-615 (2007)), however, despite showing potency in preclinical evaluation and clinical trials, both cardiotoxicity and undesirable effects on the normal vasculature are reported for these agents (Lippert J W, Bioorg Med Chem, 15, 605-615 (2007); Beerepoot et al., J Clin Oncol, 24, 1491-1498 (2006); Rustin et al., J Clin Oncol, 21, 2815-2822 (2003)).

The present inventors have developed a system for overcoming the toxic effect of systemic administration of certain potent anti-cancer agents such as vascular disrupting agents.

STATEMENTS OF THE INVENTION

According to a first aspect of the invention there is provided a compound, or pharmaceutically acceptable salt thereof, comprising a vascular disrupting agent (VDA) associated with a MMP proteolytic cleavage site. The term "associated with" in the context of the invention is intended to include all direct and indirect means of association, generally covalent, including, but not limited to, chemical cross-linking or peptide bond linkage.

Pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

In a preferred aspect the invention provides a compound of formula (I)

wherein
X is a vascular disrupting agent (VDA);
Y is a matrix metalloproteinase (MMP) proteolytic cleavage site.

Compounds according to the invention provide prodrugs which are converted to an active and potent VDA within the tumour environment by overexpressed MMPs. Tumour selective activation of a prodrug of the invention increases tumour levels, and decreases systemic levels, of the VDA and optionally additional active ingredients thereby greatly increasing their therapeutic index and efficacy.

VDAs comprise a multi-ring system, for example a fused or unfused bicyclic or tricyclic ring system. Thus X includes any multi-ring system of a VDA that is capable of binding to and disrupting tumour blood vessels.

VDAs are compounds which directly interact with tubulin and consequently intracellular microtubules, resulting in a cytostatic or cytotoxic effect. VDAs can be divided into three classes:
  (i) those compounds that interact with tubulin at the colchicine binding site on tubulin;
  (ii) those compounds that share a common binding site on tubulin with the Catharanthus (Vinca) alkaloids;
  (iii) compounds that promote the formation of stable microtubules in a manner similar to paclitaxel, a novel taxane diterpenoid isolated from the bark of the Pacific yew.

Thus in a preferred aspect of the invention the VDA is a tubulin binding agent. The tubulin binding agent may be selected from the group consisting of i) those which interact with tubulin at the colchicine binding site: including but not limited to colchicine (including colchicine analogues such as N-acetylcolchinol-O-phosphate (ZD6126) and ABT-751), colchicinoids, combretastatins, phenstatin, podophyllotoxins, steganacins, amphethinile and stilbenes. and ii) those which interact with the Vinca binding site of tubulin: including but not limited to vincristine, vinblastine, vinflunine, maytansinoids, phomopson A, rhizoxin, auristatin (including analogues thereof) and dolastatin In a yet preferred aspect of the invention the VDA is a tubulin binding agent that interacts with the colchicine binding site within tubulin.

Colchicine derivatives may include, but are not limited to, azademethylcolchicine, azacolchicine, N-methyl desacetylcolchicine, desacetylcolchicine.

The VDA may include tubulin binding agents including combretastatins (e.g. combretastatin A-4 3-0-phosphate), auristatin (including analogues thereof), dolastatin; and flavenoids (e.g. tumour necrosis factor α and 5,6-dimethylxanthenone-4-acetic acid (DMXAA), flavone acetic acid (FAA)). Thus in an alternative embodiment of the invention the VDA is a combretastatin.

The invention includes any member of the MMP family. Proteolytic cleavage at the MMP cleavage site by an MMP releases the VDA, and any other active agent associated with the MMP cleavage site, in active form.

The MMP family is divided into eight structural groups: five of which are secreted and three which are membrane-type MMPs (MT-MMPs). MT-MMPs are localised on the cell surface. The invention includes secreted MMPs and membrane type MMPs.

In a preferred aspect of the invention the MMP is a membrane-type (MT-MMP). The MT-MMP may be selected from the group consisting of
  (i) type I transmembrane type MT-MMPs for example MMP-14 (MT1-MMP), MMP-15 (MT2-MMP), MMP-16 (MT3-MMP) and MMP-24 (MT5-MMP);
  (ii) glycosyl phosphatidylinositol (GPI)-anchored structural group of MT-MMPs for example MMP-17 (MT4-MMP) and MMP-25 (MT6-MMP);
  (iii) type II transmembrane class for example MMP-23. The invention also encompasses any MMP proteases subsequently identified and classified into one of these MT-MMP subfamilies.

The MMP cleavage site may comprise any peptide sequence having an amide bond, typically a peptide bond, that is cleavable by a MMP. Preferably Y is a peptide sequence comprising between two and twenty amino acids, for example between four and ten amino acids (e.g. 7 or 8 amino acids). The amino acids of the peptide sequence may include any naturally occurring or synthetic D- or L-amino acid, preferably L- or combinations of D- and L-amino acids.

The invention also includes peptide analogues, for example peptide mimics, of the peptide sequence in which for example an amide bond is replaced with olefinic bonds, Nα- and Cα-methylated amino acids, unnatural amino acids and other approaches known in the art. Such peptidomimetic approaches are used in the art to enhance the specificity of cleavage thereby serving to diminish undesired enzymatic hydrolysis.

In a preferred embodiment of the invention the MMP proteolytic cleavage site comprises a sequence of amino acids (e.g. 6 to 10 amino acids) in which one or more amino acids in the sequence namely serine, threonine and/or tyrosine are glycosylated to enhance hydrophilicity and as such solubility. O-glycosylation of suitable amino acids in the sequence namely serine, threonine and tyrosine may enhance hydrophilicity and as such solubility. Preferably the MMP proteolytic cleavage site comprises 8 amino acids.

The MMP proteolytic cleavage site may comprise the sequence P4-P3-P2-P1-P1'-P2'-P3'-P4'
wherein P1 to P4 and P1' to P4', which may be the same or different, are amino acid residues and wherein proteolytic cleavage takes place between residues P1 and P1'. Preferably P1 and P1' are different. Preferably still P1 to P4 are different. Preferably P1' to P4' are different.

In one embodiment P1 is Gly and/or P1' is Hof.

The MMP proteolytic cleavage site may comprise the amino acid sequence (i)
-Cit-Gly-Hof-Tyr-Leu- (SEQ ID NO: 1)

In an embodiment of the invention the MMP proteolytic cleavage site comprises the amino acid sequence (ii)
-K-K-Cit-Gly-Hof-Tyr-Leu- (SEQ ID NO: 2)
wherein K represents an amino acid which may be selected from the group consisting of, but not limited to, Cit, Gly, Glu and Pro.

In an embodiment of the invention the MMP proteolytic cleavage site comprises the amino acid sequence (iii)
-Glu-Pro-Cit-Gly-Hof-Tyr-Leu- (SEQ ID NO: 3)

In a preferred embodiment the MMP proteolytic cleavage site comprises the amino acid sequence (iv)
-Arg-Ser-Cit-Gly-Hof-Tyr-Leu- (SEQ ID NO: 4)

An embodiment the invention comprises a compound of formula (I) wherein Y comprises a C-terminal site and an N-terminal site and wherein said C-terminal site is directly or indirectly linked to X and said N-terminal site is directly or indirectly linked to a further moiety for example c or Z as described hereinbelow.

An alternative embodiment of the invention comprises a compound of formula (I) wherein Y comprises a C-terminal site and an N-terminal site and wherein said N-terminal site is directly or indirectly linked to X and said C-terminal site is directly or indirectly linked to a further moiety for example c or Z as described hereinbelow.

In one preferred embodiment the invention there is provided a compound of formula (I) wherein X is colchicine or an analogue thereof and Y is a peptide comprising the amino acid sequence -Arg-Ser-Cit-Gly-Hof-Tyr-Leu- (SEQ ID NO: 4).

In a preferred aspect the invention provides a compound of formula (II)

$$X\text{—}Y\text{-}c \qquad (II)$$

wherein X and Y are as defined herein;
c is an end group or "capping group". Capping groups may be used to cap a peptide chain in pharmaceutical use in order to prevent non-specific degradation of the peptide for example by enzymes other than MMPs. c may include any appropriate moiety on the N- or C-terminus acting as a blocking group including, but not limited to simple sugars, D-amino acids, proline imino acids or fluorescein derivatives.

The present invention may further provide a "linker". The linker may be provided at the C and/or N terminus of Y. Preferably the linker is provided at the C terminus of Y. Preferably the linker is continuous with the amino acid sequence of Y. The linker may include any moiety that is associated with Y and which may be removed chemically, enzymatically or decompose spontaneously. The linker may consist of a single amino acid (e.g. tyrosine) or may comprise an amino acid sequence. Where the linker comprises a sequence of amino acids, the sequence may provide a hydrophilic region that may facilitate cleavage by an MMP at Y. O-glycosylation of suitable amino acids in the sequence namely serine, threonine and tyrosine may enhance hydrophilicity and as such solubility.

Thus in a preferred aspect of the invention there is provided a compound of formula (III)

wherein X and Y are as defined herein; and
a is a linker wherein the linker is directly or indirectly associated with X.

In an embodiment the invention provides a compound of formula (IV)

wherein X, a, Y and c are as defined herein.

In a yet further preferred aspect of the invention there is provided a "spacer" which may be the same as, or different to, the linker described herein. The spacer may be provided at the C and/or N terminal of Y. Preferably the spacer is provided at the N terminus of Y and serves to prevent unwanted removal of c during synthesis. The spacer may be directly or indirectly associated with Y. The spacer may include any single amino acid (e.g. β-alanine), amino acid sequence, a succinyl group. Thus the invention preferably provides a compound of formula (V)

wherein X, Y, and c are as defined herein;
b is a spacer as defined herein.

In a further embodiment the invention provides a compound of formula (VI)

wherein X, Y, a, b and c are as defined herein.

In one embodiment of the invention there is provided a compound of formula (VI) wherein X is colchicine (or an analogue thereof), Y is a peptide comprising the amino acid sequence -Arg-Ser-Cit-Gly-Hof-Tyr-Leu- (SEQ ID NO: 4), a is tyrosine, b is alanine and c is fluorescein or a derivative thereof.

In a second aspect of the invention there is provided a compound, or pharmaceutically acceptable salt thereof, of formula (VII)

wherein X and Y are as defined herein; Z is an anti-cancer agent.

Preferably Z is an anticancer agent selected from the group consisting of a vascular disrupting agent (preferably different to X), an antimetabolite (e.g. 5-fluorouracil), a cytotoxic or antiproliferative agent (e.g. anthracycline (e.g. doxorubicin), vinca alkaloid, taxane, cytotoxic nucleotide), a biotoxin, radiotherapeutic, hormonal agent or any natural products or agents known to induce a cytotoxic, cytostatic, anti-angiogenic or vascular disrupting effect.

In a preferred aspect of the invention there is provided a compound of formula (VIII)

wherein X, a, Y and Z are as defined herein.

In a yet preferred aspect of the invention there is provided a compound of formula (IX)

wherein X, a, Y, b and Z are as defined herein. In this aspect of the invention, the purpose of the spacer b is to convert the N-terminal amine of Y into a carboxylic acid to allow attachment of a compound Z wherein Z bears a free amine (for example where Z is doxorubicin). Where Z bears a free carboxylic acid, b is not required.

In one preferred embodiment the invention there is provided a compound of formula (VII) wherein X is colchicine (or an analogue thereof) and Z is doxorubicin. Preferably still Y is a peptide comprising the amino acid sequence -Arg-Ser-Cit-Gly-Hof-Tyr-Leu- (SEQ ID NO: 4).

The extent of protection includes counterfeit or fraudulent products which contain or purport to contain a compound of the invention irrespective of whether they do in fact contain such a compound and irrespective of whether any such compound is contained in a therapeutically effective amount.

Included in the scope of protection are packages which include a description or instructions which indicate that the package contains a species or pharmaceutical formulation of the invention and a product which is or comprises, or purports to be or comprise, such a formulation or species. Such packages may be, but are not necessarily, counterfeit or fraudulent.

A further aspect of the invention provides a process for preparing a compound according to the invention the process comprising the steps of
i) providing a solid support attached to X;
ii) optionally attaching a linker a to the C or N terminal of X;
iii) attaching amino acid residues step-wise to the C or N terminal of X, or the linker attached to X in (ii), to provide the peptide sequence Y containing the MMP proteolytic cleavage sequence;
iii) optionally attaching a capping group c to the respective C or N terminal of Y to provide a compound of formula (II) or (IV).

In a preferred process the solid support is any polymeric support such as any polystyrene based or PEG based resin for example trityl-based resins.

In a further aspect the invention provides the use of a MMP proteolytic cleavage site in the site specific activation of a VDA. The term "site specific activation" as used herein means, in general terms and not limited to, the activation of a VDA by site specific cleavage at the MMP proteolytic cleavage site. Site specific cleavage at the proteolytic cleavage site is expected to take place concomitantly with the release and hence activation of the VDA.

Pharmaceutical Compositions and Uses

In other aspects the invention provides a compound, or pharmaceutically acceptable salt thereof, as hereinbefore described for use in medicine. In further aspects, there is provided a pharmaceutical formulation comprising a compound as hereinbefore described. The formulation may contain at least one additional pharmaceutically acceptable component e.g. an excipient, diluent or carrier. Preferably the formulation is intended for parenteral administration.

The invention provides a pharmaceutical formulation comprising a compound according to the invention. In a preferred embodiment, the compound is of formula (VII).

In a preferred aspect of the invention said composition includes a pharmaceutically acceptable carrier or diluent.

The compositions of the invention are typically administered in effective amounts. An "effective amount" is that amount of a composition that alone, or together with further doses, produces the desired response. When administered, the pharmaceutical compositions of the present invention are administered in pharmaceutically acceptable preparations. Such preparations may routinely contain pharmaceutically acceptable concentrations of salt, buffering agents, preservatives, compatible carriers and optionally other therapeutic agents (for example, cisplatin; carboplatin; cyclosphosphamide; melphalan; carmusline; methotrexate; 5-fluorouracil; cytarabine; mercaptopurine; daunorubicin; doxorubicin; epirubicin; vinblastine; vincristine; dactinomycin; mitomycin C; taxol; L-asparaginase; G-CSF; etoposide; colchicine; derferoxamine mesylate; and camptothecin).

The compositions of the invention can be administered by any conventional route, including injection or by gradual infusion over time. The administration may, for example, be oral, intravenous, intraperitoneal, intramuscular, intracavity, subcutaneous, or transdermal. In the case of treating a particular disease, such as cancer, the desired response is inhibiting the progression of the disease. This may involve only slowing the progression of the disease temporarily, although more preferably, it involves halting the progression of the disease permanently. This can be monitored by routine methods known in the art.

Administration of the compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients.

Pharmaceutical compositions may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal. Compositions suitable for oral administration may be presented as discrete units, such as capsules, tablets, lozenges, each containing a predetermined amount of the active compound. Other compositions include suspensions in aqueous liquids or non-aqueous liquids such as syrup, elixir or an emulsion.

Compositions suitable for parenteral administration conveniently comprise a sterile aqueous or non-aqueous preparation of compound, which is preferably isotonic with the blood of the recipient. This preparation may be formulated according to known methods using suitable dispersing or wetting agents and suspending agents. The sterile injectable preparation also may be a sterile injectable solution or suspension in a nontoxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

In an aspect of the invention, the compounds according to the invention may be used to treat a disease or condition associated with tissue expressing an MMP, particularly a cancer.

The invention provides a method to treat cancer in a subject comprising administering an effective amount of a compound according to the invention. In a preferred method of the invention said subject is human.

As used herein, the term 'cancer' refers to cells possessing the capacity for autonomous growth i.e., an abnormal state or condition characterised by rapidly proliferating cell growth. The term is meant to include all types of cancerous growths or oncogenic processes, metastatic tissues or malignantly transformed cells, tissues, or organs, irrespective of histopathological type or stage of invasiveness. The term 'cancer' includes malignancies of epithelial, endodermal and mesenchymal origin, particularly carcinomas and sarcomas, such as those affecting the respiratory system (mouth, nose, trachea, lung), gastrointestinal tract (tongue, esophagus, stomach, small intestines, colon, liver, pancreas, gall bladder, rectum), endocrine system (thyroid, pituitary, adrenal glands), genitourinary tract (urinary bladder, kidney), reproductive system (breast, ovaries, uterus, cervix, prostate, penis, scrotum, testes), skin (melanocytes, epidermis, endodermis), nervous system (brain, spinal cord, glial cells, neurons) and lymphoid system.

The term 'carcinoma' is art recognised and refers to malignancies of epithelial origin including respiratory system carcinomas, gastrointestinal system carcinomas, endocrine system carcinomas, genito-urinary tract carcinomas, skin carcinomas, and carcinomas of the reproductive system. The term "carcinoma" also includes "adenocarcinomas" referring to carcinomas deriving from glandular tissue, "squamous carcinomas" referring to carcinomas of squamous origin, and "carcinosarcomas" referring to tumours composed of carcinomatous and sarcomatous tissue. Exemplary carcinomas include those forming from the epithelia of the cervix, prostate, breast, nose, head and neck, oral cavity, esophagus, stomach, liver, pancreas, colon, ovary, urinary bladder and lung, particularly non-small lung carcinoma.

The term 'sarcoma' is art recognised and refers to malignancies of soft tissues or connective or supportive tissue, including bone, cartilage, adipose tissue, smooth muscle, skeletal muscle, nerve sheath, blood vessels, mesothelium, and gastrointestinal stroma. Further types of cancer include "leukaemias" which refer to tumours deriving from white blood cells, and "lymphomas" referring to tumours of the lymphoid system.

A pharmaceutical formulation comprising a compound according to the invention may be administered in combination, either sequentially or at a substantially similar time, as an anti-cancer agent including, but not limited to, an antimetabolite (e.g. 5-fluorouracil), a cytotoxic or anti-proliferative agent (e.g. anthracycline, vinca alkaloid, taxane, cytotoxic nucleotide), a biotoxin, radiotherapeutic, hormonal agent or any natural products or agents known to induce a cytotoxic, cytostatic, anti-angiogenic or vascular disrupting effect.

As used herein, "treatment" refers to clinical intervention in an attempt to alter the natural course of the individual or cell being treated, and may be performed either for prophylaxis or during the course of clinical pathology.

In a further aspect the invention provides the use of a compound according to the invention in the manufacture of a medicament to treat cancer.

In one aspect of the present invention the compounds or compositions of the invention may be used to treat an inflammatory disorder and/or an inflammatory response. Thus, according to a further of the invention there is provided a method to treat an inflammatory disorder in a subject comprising administering an effective amount of a compound according to the invention.

The inflammatory disorder may be selected from the group consisting of consisting of atherosclerosis, rheumatoid arthritis, osteoarthritis, gout, lupus erythematosus, scleroderma, Sjorgen's syndrome, poly- and dermatomyositis, vasculitis, tendonitis, synovitis, bacterial endocarditis, periodontitis, osteomyelitis, psoriasis, pneumonia, fibrosing alveolitis, chronic bronchitis, bronchiectasis, emphysema, silicosis, pneumoconiosis, tuberculosis, ulcerative colitis, Crohn's disease, chronic inflammatory demyelinating polyradiculoneuropathy, chronic inflammatory demyelinating polyneuropathy, multiple sclerosis, Guillan-Barre Syndrome and myasthemia gravis, mastitis, laminitis, laryngitis, chronic cholecystitis, Hashimoto's thyroiditis, and inflammatory breast disease. In one embodiment, the inflammatory disorder may be the result of tissue or organ rejection after transplantation. In particular embodiments, the inflammatory disorder is selected from the group consisting of atherosclerosis, rheumatoid arthritis, osteoarthritis, sepsis and polyarthritis.

The compounds of the invention may be used to treat heart failure. Also provided is a use of a compound as described herein for the manufacture of a medicament to treat heart failure.

In one embodiment of the present invention the compounds of the invention may be useful in treating a wound (e.g. ulcers, lesions including cutaneous cuts or burns). Thus the invention provides a method to treat a wound in a subject comprising administering an effective amount of a compound according to the invention. In a preferred method of the invention said subject is human.

The compounds of the invention may also be used to treat conditions and disorders associated with menstruation.

There is further provided a package or kit of parts comprising:
(1) a compound or composition described herein; together with
(2) instructions to use the compound in a method or use described herein.

The package defined herein may comprise more than one dosage unit in order to provide for repeat dosing. If more than one dosage unit is present, such units may be the same, or may be different in terms of the dose of the compound composition and/or physical form.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described 5 in conjunction with a particular aspect, embodiment or example of the invention are to be understood to be applicable to any other aspect, embodiment or example described herein unless incompatible therewith.

The invention will now be described by way of example only with reference to the following Figures in which.

EXAMPLE

Materials and Methods

Synthesis of Immobilised Colchicine Derivative

Synthesis of 1:

Ammonia solution (35%, 15 mL) was added to colchicine (750 mg, 1.88 mmol, 1.00 eq) and the reaction mixture stirred at room temperature overnight. The crude product was washed with KHSO$_4$ (1 M, aq), dried with MgSO$_4$, filtered and concentrated under reduced pressure. It was subsequently purified by flash chromatography on silica gel (gradient elution: CH$_2$Cl$_2$/methanol 95:5 to 10:1) to give 1 as a yellow solid (427 mg, 1.11 mmol, 59%). $\delta_H$ (600 MHz, CDCl$_3$), 7.99 (1H, broad s, NH), 7.56 (1H, d, J 2.1, C8-H), 7.32 (1H, d, J 10.7, C11-H), 6.88 (1H, d, J 11.0, C10-H), 6.52 (1H, s, C4-H), 6.03 (2H, broad s, NH$_2$), 4.68 (1H, ddd, J 12.6, 6.5 and 6.5, C7-H), 3.93 (3H, s, OCH$_3$), 3.88 (3H, s, OCH$_3$), 3.60 (3H, s, OCH$_3$), 2.47 (1H, dd, J 13.4 and 6.2, C5-CH$_2$), 2.35 (1H, ddd, J 13.4, 12.7 and 6.9, C5-CH$_2$), 2.29-2.23 (1H, m, C6-CH$_2$), 1.98 (3H, s, CH$_3$), 1.90-1.88 (1H, m, C6-CH$_2$); ES m/z (%) 385 [M$^+$+H] (100).

Synthesis of 2:

HCTU (642 mg, 1.55 mmol, 1.50 eq) and diisopropylethylamine (DiPEA, 516 μL, 404 mg, 3.11 mmol, 3.00 eq) were added to a solution of Fmoc-tyr(tBu)-OH (714 mg, 1.55 mmol, 1.50 eq) in DMF (10 mL). After stirring at room temperature for 5 minutes, 1 (398 mg, 1.04 mmol, 1.00 eq) was added to the solution. The reaction mixture was stirred at 50° C. for 22 h. DMF was removed in vacuo and the resultant oil was dissolved in CH$_2$Cl$_2$ (20 mL). The organic phase was washed with KHSO$_4$ (aq, 2×20 mL), dried with MgSO$_4$ and concentrated under reduced pressure. The crude product was purified by flash chromatography (gradient elution: CH$_2$Cl$_2$/methanol 100:0 to 99:1 to 98:2) to give 2 as a yellow solid (530 mg, 642 μmol, 67%).

$\delta_H$ (600 MHz, CDCl$_3$), 10.42 (1H, broad s, NH), 9.02 (1H, d J 10.7, C11-H), 7.75 (2H, d, J 7.2, C23-H, C24-H), 7.54 (2H, d, J 7.2, C20-H, C27-H), 7.45 (1H, d, J 11.0, C10-H), 7.39 (2H, dd, J 7.2 and 7.2, C22-H, C25-H), 7.29 (2H, dd, J 6.6 and 6.6, C21-H, C26-H), 7.19 (1H, broad s, C8-H), 7.03 (2H, d, J 7.9, C14-H, C17-H), 6.81 (2H, d, J 7.9, C15-H, C16-H), 6.50 (1H, s, C4-H), 5.88 (1H, broad s, NH), 5.25 (1H, broad s, C12-H), 4.73-4.67 (1H, m, C7-H), 4.43 (1H, dd, J 10.0 and 7.6, C18-CH$_2$), 4.28 (1H, dd, J 10.0 and 7.2, C18-CH$_2$), 4.16 (1H, dd, J 7.2 and 6.19, C19-H), 3.93 (3H, s, OCH$_3$), 3.88 (3H, s, OCH$_3$), 3.62 (3H, s, OCH$_3$), 3.21 (1H, dd, J 13.1 and 4.8, C13-CH$_2$), 3.11 (1H, dd, J 13.1 and 5.5, C13-CH$_2$), 2.53 (1H, dd, J 13.4 and 6.2, C5-CH$_2$), 2.40 (1H, ddd, J 13.4, 12.7 and 6.9, C5-CH$_2$), 2.22-2.15 (1H, m, C6-CH$_2$), 1.88 (3H, s, CH$_3$), 1.80 (1H, ddd, J 11.5, 11.3 and 6.9, C6-CH$_2$), 1.22 (9H, s, C(CH$_3$)$_3$); ES m/z (%) 826 [M$^+$] (100).

Synthesis of 3:

TFA (2 mL) was added to a solution of 2 (486 mg, 589 μmol, 1.00 eq) and the reaction mixture stirred for 20 min. TLC indicated quantitative conversion to the product. The product was concentrated under reduced pressure, with toluene co-evaporation to give 3 in quantitative yield.

$\delta_N$ (600 MHz, CDCl$_3$), 10.08 (1H, broad s, NH), 8.99 (1H, d J 10.7, C11-H), 7.71 (2H, d, J 6.2, C23-H, C24-H), 7.55 (1H, s, C8-H), 7.49 (2H, dd, J 6.5 and 6.5, C20-H, C27-H), 7.41 (1H, d, J 10.2, C10-H), 7.33 (2H, dd, J 6.2 and 6.2, C22-H, C25-H), 7.26-7.21 (2H, m, C21-H, C26-H), 6.91 (2H, d, J 8.3, C14-H, C17-H), 6.56 (2H, d, J 7.2, C15-H, C16-H), 6.45 (1H, S, C4-H), 5.93 (1H, broad s, NH), 5.28 (1H, s, NH), 4.95-4.90 (1H, m, C12-H), 4.60 (1H, ddd, J 11.7, 5.8 and 6.9, C7-H), 4.39 (1H, dd, J 8.9 and 8.6, C18-CH$_2$), 4.29-4.24 (1H, m, C18-CH$_2$), 4.12 (1H, dd, J 6.9 and 6.9, C19-H), 3.90 (3H, s, OCH$_3$), 3.84 (3H, s, OCH$_3$), 3.54 (3H, s, OCH$_3$), 3.08 (2H, d, J 5.2, C13-CH$_2$), 2.44 (1H1 dd, J 13.4 and 6.2, C5-CH$_2$), 2.33-2.26 (1H, m, C5-CH$_2$), 2.15-2.09 (1H, m, C6-CH$_2$), 1.82 (3H, s, CH$_3$), 1.75-1.69 (1H, m, C6-CH$_2$); ES m/z (%) 770 [M$^+$] (100).

Preparation of 4:

2-Chlorotrityl chloride resin (Novabiochem, 100-200 mesh, substitution 1.4 mmolg$^{-1}$, 589 mg, 0.765 mmol, 1.00 eq) was suspended in a solution of 3 (589 mg, 0.765 mmol, 1.00 eq), dimethylaminopyridine (10 mg, 76.5 μmol, 0.01 eq), DiPEA (247 mg, 1.913 mmol, 333 μL, 2.50 eq) and pyridine (241 mg, 3.061 mmol, 248 μL, 4.00 eq) in THF (10 mL) and stirred for 6 hours at 50° C. The resin was subsequently filtered and washed thoroughly with THF. The resin was then capped by washing the resin carefully with methanol (CH$_2$Cl$_2$:MeOH:DiPEA 17:2:1, 100 mL). Resin 4 was dried overnight over P2O5. Dry resin weight: 593 mg (loading 56%).

General Procedure for Synthesis of Endopeptidase-Activated Pro-Drugs fluo-bala-glu-pro-cit-gly-hof-tyr-leu-tyr-colch (SEQ ID NO: 5)

As an example, peptide conjugate 5 was synthesised using conventional solid phase peptide synthesis, from immobilised colchicine derivative 4, using an Fmoc-based strategy.

$N^\alpha$-Fmoc strategy synthesis of peptide acids was achieved manually using 2-chlorotrityl-derivatised resin 4. The resin was swelled thoroughly in DMF, followed by removal of the N-Fmoc protecting group by treatment with 20% v/v piperidine in DMF (3×3 min). All couplings were performed in DMF, employing 2.5-fold molar excesses of $N^\alpha$-Fmoc protected amino acids (with appropriate side-chain protecting groups), and activated using HCTU/HOBt/DiPEA. $N^\alpha$-Fmoc deprotections were performed using 20% piperidine in DMF (3×3 min). The success of couplings and de-protections was monitored using the ninhydrin-based Kaiser test. Unsuccessful couplings were repeated. After the final $N^\alpha$-Fmoc deprotection, the peptide chain was endcapped with fluorescein isothiocyanate (2.50 eq, in the presence of DiPEA1 1.50 eq). The success of this reaction was also monitored by the Kaiser test.

An additional β-alanine residue was incorporated into the sequence to overcome incompatibility of the thiourea linkage and the acidic conditions of cleavage (the thiourea can rearrange, and the carbonyl carbon of the preceding amide bond can undergo nucleophilic attack by the sulphydryl-like function so formed. This leads to cleavage of the amide bond, with concomitant formation of a cyclic thiazolinone. The thiazolinone can undergo rearrangement in the presence of aqueous acid to form a thiohydantoin).

On completion of the sequence, the resin was washed (DMF, CH2Cl2, CH2Cl2/MeOH) and dried in vacuo over KOH to constant weight. Peptides were cleaved from the resin by mild acidolysis using TFA-H2O-triisopropylsilane 95:2.5:2.5 for 2 h at RT, with simultaneous side-chain de-protection. Following cleavage, the TFA was removed under reduced pressure. The crude product was extracted into 95% aqueous acetic acid and lyophilised. The crude peptide was subsequently analysed using reversed phase HPLC and purified using preparative HPLC (purity>97%). Pure fractions were combined and lyophilised. Identity was confirmed by mass spectrometry.

Potential Attachment of Parent Colchicine to a Peptide Sequence Through the B-Ring To enable attachment of a colchicine moiety through the peptide N-terminus, the following strategy will be used. The B-ring amine can be de-masked using published methods. Acylation with aspartic acid will introduce a carboxylic acid to the molecule (from the amino acid side chain) thereby enabling conjugation to the free amine at the peptide N-terminus (see below).

Acetylation of the amide bond will also be examined, to assess whether parent colchicine is released following MMP activation and subsequent exopeptidase degradation.

Strategies for the Attachment of Doxorubicin to a Peptide Sequence

To enable attachment of doxorubicin through the peptide N-terminus (following peptide synthesis using the immobilised colchicine derivatised resin previously described) it must first be modified to introduce a carboxylic acid. Examples include reaction with succinic anhydride (strategy 1, below). However, by utilising the side chain of aspartic acid (both natural amino acids), as shown below (strategy 2) a natural amino acid (as opposed to a foreign chemical entity) is released on metabolism:

Strategy 1: (Succinyl Spacer)

Strategy 2: (Amino Acid Spacer)

L-Asp(OtBu)-OH

+ attachment to peptide N-terminus

C-Terminal Doxorubicin Linkage

Protection of the amine group of doxorubicin with Dde (a commonly used protecting group in peptide chemistry and by our group) would allow immobilisation of the agent onto a trityl-based (or otherwise) resin. Subsequent removal of the Dde group would de-mask the amine, allowing a peptide sequence to be constructed from this point (i.e. through the C-terminus). Standard Fmoc-based solid phase synthesis would produce a peptide sequence. An appropriately derivatised VDA could then be conjugated through the N-terminus. Resin cleavage and purification would be as previously described.

Incorporation of Glycosylated Amino Acids (to Enhance Physicochemical Properties)

Amino acids with appropriate side chain functionality (e.g. serine, tyrosine, threonine) can be glycosylated (with mono-, di- or trisaccharides) to produce peptides with enhanced aqueous solubility. Such a carbohydrate-derivatised moiety could be used in place of serine, for example (see scheme below).

-continued

→ incorporation into peptide sequence

Figure 2:
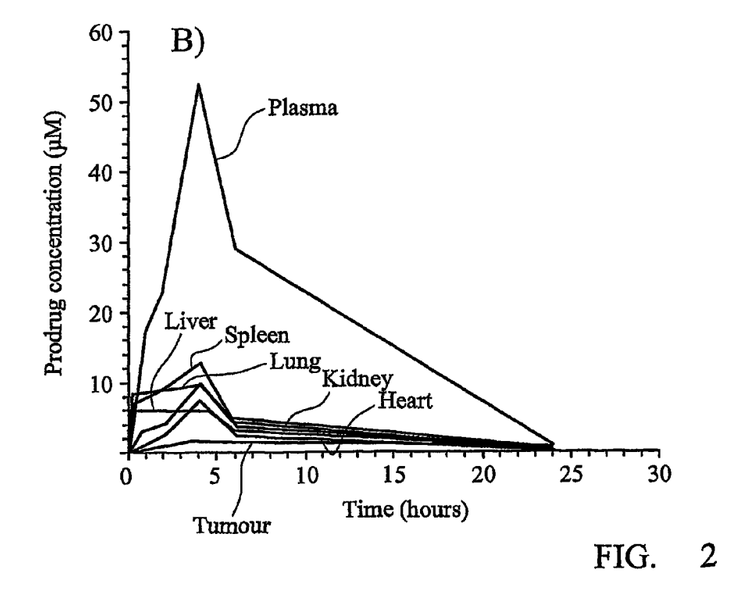
FIG. 2 is a graph showing accumulation and levels of prodrug-1 in tumour-bearing mice following intraperitoneal administration.

Results
1) MMP-Activated Prodrug (Compound i)
   Pan MMP Targeted
Structure:

b) Prodrug-1 is cleaved rapidly at the Glycine-Homophenylalanine (Gly-Hof) by recombinant MMP-2, MMP-9, MMP-10 and MMP-14 at least. Demonstrated by LC/MS/MS and mass spectrometry (data not shown)
c) Prodrug-1 was administered in vivo via the intraperitoneal route to mice bearing subcutaneous HT1080 tumour model (expression of majority of MMPs). Plasma, tissues and tumours were collected at regular intervals post-dosing. Levels of prodrug and VDA2 were assessed by LC/MS/MS.
   a. Prodrug-1 accumulated and was detected in all tissues analysed (FIG. 2).
   b. Highest prodrug-1 levels were observed in the tumour (FIG. 2).

Fluorescein—Ala—Glu—Pro—Cit—Gly—Hof—Tyr—Leu—Tyr—VDA2   (SEQ ID NO: 6)

Figure 1:
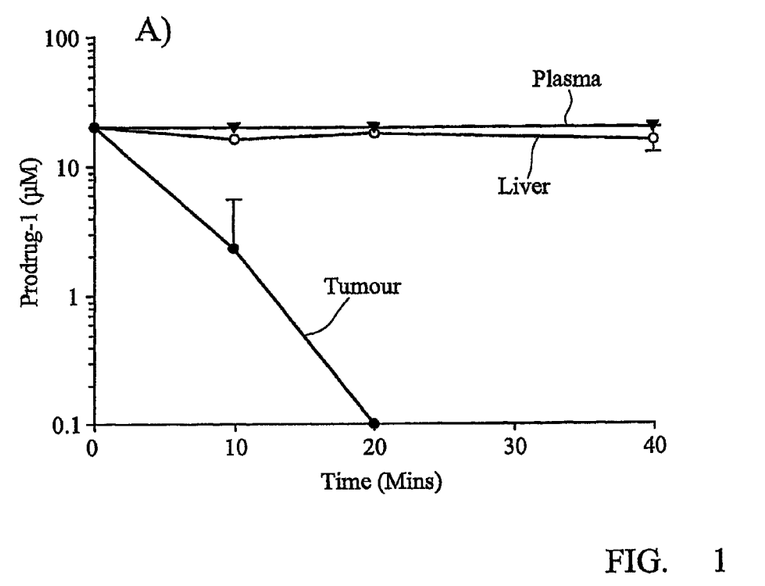
FIG. 1 is a graph showing the metabolism of prodrug-1 versus time in tumour and non-tumour tissues ex vivo.
Figure 3:
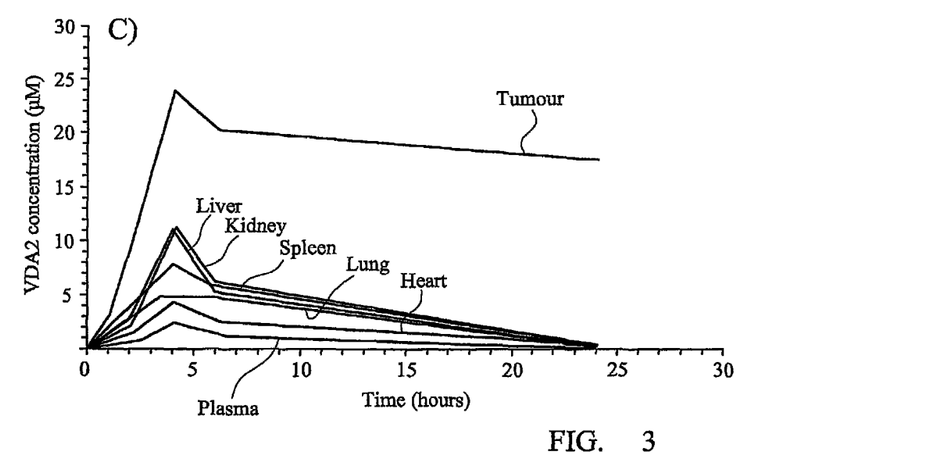
FIG. 3 is a graph demonstrating levels of VDA accumulating following intraperitoneal administration of prodrug-1 to tumour bearing mice.

(Hof = homophenylalanine; Cit = citrulline)

a) Prodrug-1 has been screened using normal mouse plasma, normal mouse liver homogenate and experimental human tumour model homogenate (HT1080 xenograft; known to express majority of MMPs) ex vivo. Prodrug cleavage and metabolism were detected using LC/MS/MS.
   a. Prodrug-1 was stable in plasma and liver, supporting systemic stability of these therapeutics (FIG. 1).
   b. Prodrug-1 was metabolised in tumour homogenate, supporting activation of these therapeutics in tumours expressing MMPs (FIG. 1).
   c. Prodrug-1 not detectable after 24 hours post-dosing. (FIG. 2)
   d. VDA2 was detectable at low levels in normal tissues following prodrug-1 administration (FIG. 3)
   e. VDA2 levels were detected at high levels in tumour tissue following prodrug-1 administration (FIG. 3)
   f. VDA2 was still detectable at high levels in tumour and was undetectable in normal tissues after 24 hours post-dosing with prodrug-1 (FIG. 3)

Figure 4:
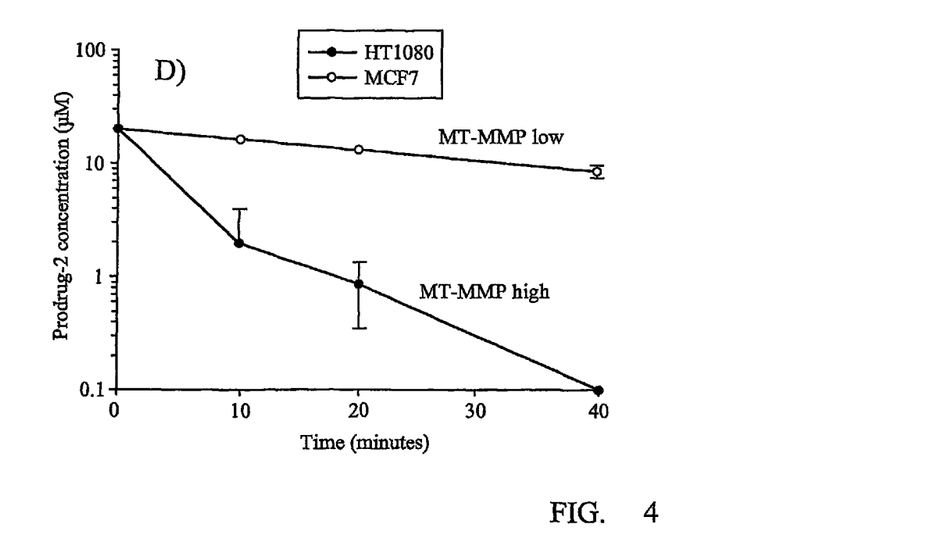
FIG. 4 is a graph showing differential metabolism of prodrug-2 in tumour homogenates expressing high MT1-MMP levels (HT1080) versus tumour homogenates expressing low MT1-MMP levels (MCF-7)
Figure 5:
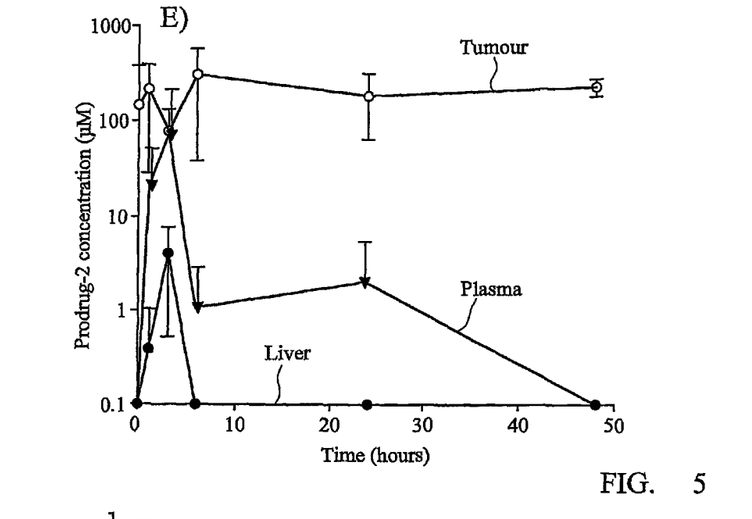
FIG. 5 is a graph showing accumulation and levels of prodrug-2 in HT1080 tumour bearing mice following intraperitoneal administration.
Figure 6:
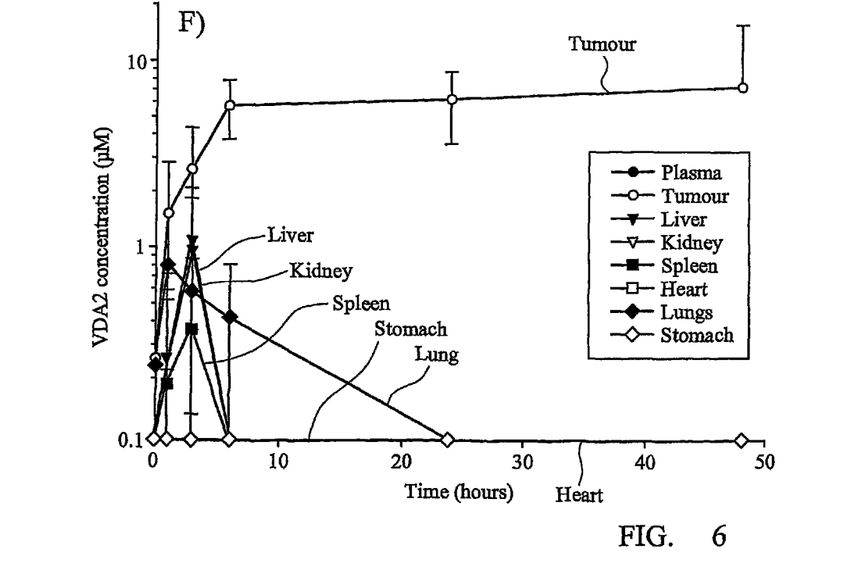
FIG. 6 is a graph demonstrating levels of VDA accumulating following intraperitoneal administration of prodrug-2 to HT1080 tumour bearing mice.

2) MMP-Activated Prodrug (Compound i)
   Targeted to Membrane-Type WIMPs (MT-MMPs)
Structure:

Fluorescein—Ala—Arg—Ser—Cit—Gly—Hof—Tyr—Leu—Tyr—VDA2  (SEQ ID NO: 7)

d) Compound 1 was modified in order to change the MMP-targeting of the compound from being pan-MMP to MT-MMP selective (Prodrug-2)
   a. Arginine was incorporated in place of the Glutamic acid at the P4 position
   b. Proline was removed and replaced with Serine at the P3 position
e) Prodrug-2 has been screened using normal mouse plasma, normal mouse liver homogenate and experimental human tumour model homogenates demonstrating high MT1-MMP (MMP-14) expression and activity (HT1080) and low MT1-MMP expression and activity (MCF-7) ex vivo. Prodrug-2 cleavage and metabolism were detected using LC/MS/MS.
   a. Prodrug-2 remained intact in plasma supporting systemic stability of this therapeutic.
   b. Prodrug-2 remained stable in murine liver homogenates
   c. Prodrug-2 was metabolised rapidly in tumour homogenate expressing high MT-MMP levels (HT1080) relative to tumour homogenate expressing low MT-MMP levels (MCF7) (FIG. 4).
   d. These data support the systemic stability of this prodrug and the selectivity of activation by MT-MMPs.
f) Prodrug-2 is cleaved differentially by MMPs as shown by LC/MS/MS and mass spectrometry (data not shown):
   a. Cleaved rapidly at the Glycine-Homophenylalanine (Gly-Hof) by recombinant MMP-14.
   b. Cleaved slowly at the Homophenylalanine-Tyrosine (Hof-Tyr) by recombinant MMP-2. Demonstrating different cleavage to that observed with prodrug-1.
   c. Prodrug-2 is not cleaved by recombinant MMP-9, in contrast to prodrug-1
   d. These data support the MMP selective cleavage of prodrug-2
g) Prodrug-2 was administered in vivo via the intraperitoneal route to mice bearing subcutaneous HT1080 tumour model (MT1-MMP positive). Plasma, tissues and tumours were collected at regular intervals post-dosing. Levels of prodrug-2 and VDA2 were assessed by LC/MS/MS.
   a. Prodrug-2 accumulated and was detected in all tissues analysed (FIG. 5).
   b. Highest prodrug-2 levels were observed in the tumour (FIG. 5).
   c. Liver was representative of all normal tissues analysed. (FIG. 5)
   d. VDA2 was undetectable in plasma following administration of prodrug-2 (FIG. 6)
   e. High concentrations of VDA2 were detected in tumour following prodrug-2 administration (FIG. 6)
   f. Levels of VDA2 in tumour were 10 times higher than that detected in normal tissues following administration of prodrug-2 (FIG. 6)
   g. High levels of prodrug-2 and VDA2 were still detectable in tumour 48 hours post administration.

The invention claimed is:

1. A method of treating cancer in a subject comprising administering to the subject an effective amount of a compound comprising a vascular disrupting agent (VDA), linked to a peptide comprising a matrix metalloproteinase-14 (MMP-14) proteolytic cleavage site comprising the amino acid sequence -Arg-Ser-Cit-Gly-Hof-Tyr-Leu- (SEQ ID NO: 4) or a pharmaceutically acceptable salt thereof.

2. The method according to claim 1 wherein the cancer is a solid tumor.

3. The method of claim 2 wherein the cancer is a carcinoma or a sarcoma.

4. The method of claim 2, wherein the cancer is selected from the group consisting of cancer of the mouth, nose, trachea, lung, tongue, esophagus, stomach, small intestines, colon, liver, pancreas, gall bladder, rectum, thyroid, pituitary, adrenal glands, urinary bladder, kidney, breast, ovaries, uterus, cervix, prostate, penis, scrotum, testes, skin, brain, spinal cord, glial cells, neurons and lymphoid system.

5. The method according to claim 1 wherein the compound is of formula (I)

$$X—Y \qquad (I)$$

wherein X is the VDA and Y is the peptide comprising a MMP proteolytic cleavage site.

6. The method according to claim 1 wherein the VDA is an anti-cancer agent.

7. The method according to claim 1, wherein the VDA has cytostatic or cytotoxic effect.

8. The method according to claim 1, wherein the VDA is selected from colchicine, a colchicine analog, colchicinoid, combretastatin, phenstatin, podophyllotoxin, steganacin, amphethinile, stilbene and flavonoid.

9. The method according to claim 1, wherein the VDA is selected from the group consisting of colchicine, azademethylcolchicine, azacolchicine, N-methyl desacetylcolchicine and desacetylcolchicine.

10. The method according to claim 1, wherein the VDA is a vincristine, vinblastine, vinflunine, maytansinoid, phomopson A, rhizoxin, auristatin, auristatin analog or dolastatin.

11. The method according to claim 1, further comprising administering to the subject an effective amount of another therapeutic agent.

12. The method of claim 11, wherein the another therapeutic agent is selected from the group consisting of cisplatin; carboplatin; cyclophosphamide; melphalan; carmustine; methotrexate; 5-fluorouracil; cytarabine; mercaptopurine; daunorubicin; doxorubicin; epirubicin; vinblastine; vincristine; dactinomycin; mitomycin C; taxol; L-asparaginase; G-CSF; etoposide; colchicine; derferoxamine mesylate; and camptothecin.

13. A method of treating cancer in a subject comprising administering to the subject an effective amount of a compound comprising a vascular disrupting agent (VDA) selected from the group consisting of colchicine, azademethylcolchicine, azacolchicine, N-methyl desacetylcolchicine and desacetylcolchicine, wherein the VDA is linked to a peptide comprising a matrix metalloproteinase-14 (MMP-14) proteolytic cleavage site comprising the amino acid sequence -Arg-Ser-Cit-Gly-Hof-Tyr-Leu- (SEQ ID NO:4) or a pharmaceutically acceptable salt thereof.

14. The method of claim 1, wherein the cancer is colorectal, lung, breast, or prostate cancer.

15. The method of claim 1, wherein the VDA is azademethylcolchicine.

16. The method according to claim 1, wherein the peptide comprises a capping group on the N- or C-terminus.

17. The method of claim 16, wherein the capping group is a simple sugar, a D-amino acid, a proline imino acid, fluorescein, or a fluorescein derivative.

* * * * *